United States Patent [19]
Hsieh

[11] Patent Number: 4,458,667
[45] Date of Patent: Jul. 10, 1984

[54] GAS WARMER

[76] Inventor: Jung H. Hsieh, No. 7, Alley 1, La. 225, Sec. 6, Chung Hsiao E. Rd., Taipei, Taiwan

[21] Appl. No.: 441,737

[22] Filed: Nov. 15, 1982

[51] Int. Cl.³ .............................................. A61F 7/08
[52] U.S. Cl. .................................. 126/208; 431/100; 431/274; 431/277; 431/328; 431/329
[58] Field of Search ................ 126/208, 204; 431/102, 431/100, 268, 274, 277, 344, 328, 329, 253, 326

[56] References Cited

U.S. PATENT DOCUMENTS

| | | | |
|---|---|---|---|
| 2,914,060 | 11/1959 | Wilcox | 126/208 |
| 3,049,117 | 8/1962 | Matoba | 126/208 |
| 3,405,704 | 10/1968 | Wintz | 126/208 |
| 3,509,866 | 5/1970 | Singleton | 126/208 X |
| 3,866,596 | 2/1975 | Gottwald et al. | 126/208 |

Primary Examiner—Samuel Scott
Assistant Examiner—Randall L. Green
Attorney, Agent, or Firm—Armstrong, Nikaido, Marmelstein & Kubovcik

[57] ABSTRACT

A gas warmer for use in cold regions which can be carried on the body and uses gas as fuel. The warmer comprises a closed container filled with gas fuel, and having igniter means similar to that of a cigarette lighter. In addition, the warmer contains a flow-controlled gas outlet pipe coupled to an external retainer for holding a roll of metallic cotton. When the igniter is lit, the metallic cotton is heated to incandescence. Gas fed to the metallic cotton heating element keeps the cotton in incandescence as long as the gas flow continues, even after the igniter is turned off.

2 Claims, 5 Drawing Figures

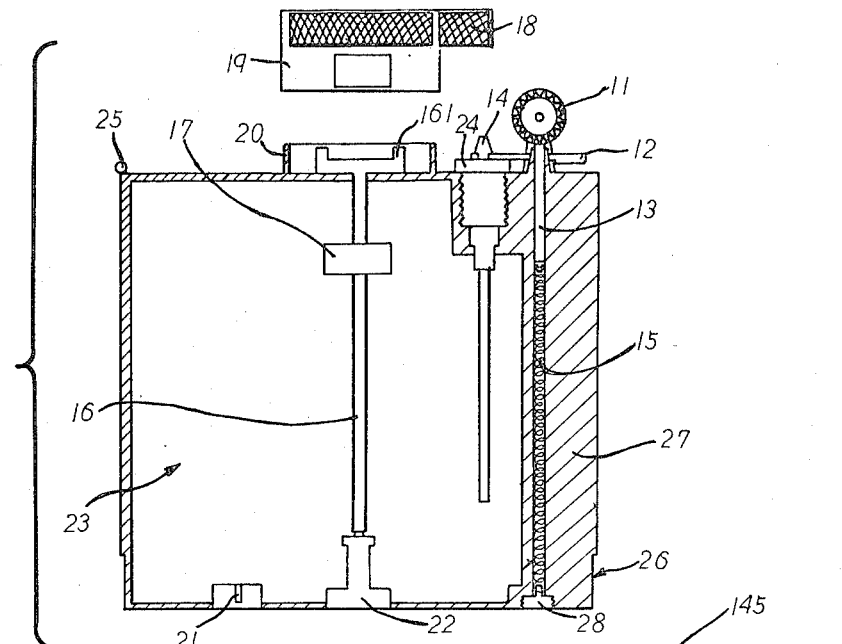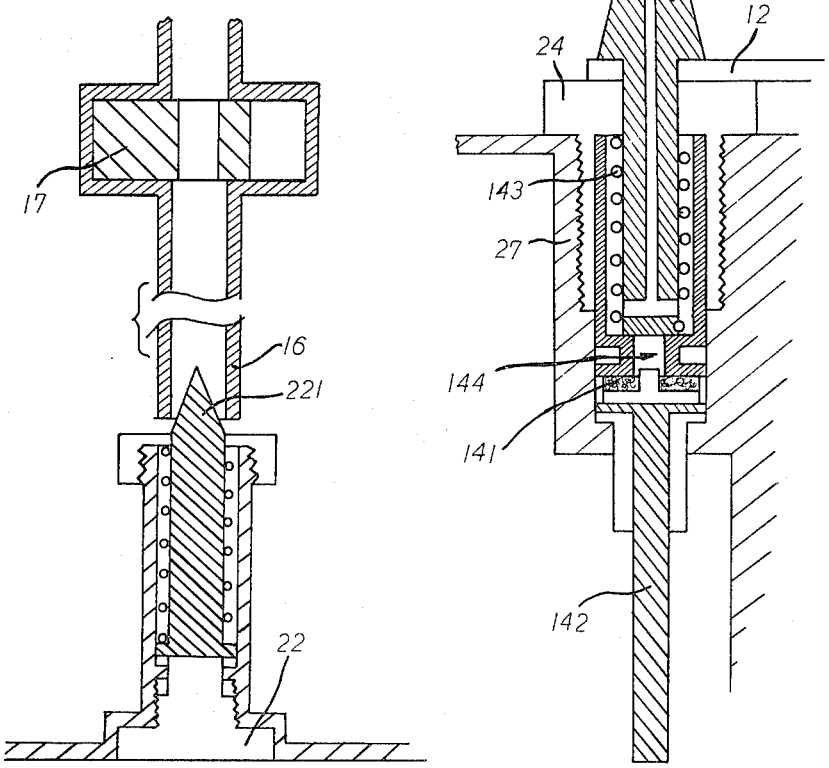
FIG.1
FIG.3  FIG.2

GAS WARMER

BACKGROUND OF THE INVENTION

This invention relates to gas heaters and especially to a portable type of gas heater which produces heat by means of incandescence rather than flame.

Conventional portable body warmers frequently are of the type which employ gasoline as a fuel source. Such warmers generally require the user to carry an ignition source, which is inconvenient. Also, gasoline is easily spilled when filling the tank and its volatility makes it very dangerous when spilled. The user must be careful about maintaining the tank in an upright position to avoid spillage. Furthermore, gasoline-powered warmers provide heat by means of a flame which can be dangerous and inconvenient.

SUMMARY OF THE INVENTION

An object of the invention is to provide a portable heater which reduces or eliminates the danger and inconveniences of gasoline-fueled heaters and substitutes incandescence for flame as the heat source.

These and other objects and advantages are attained by the present invention, which provides a gas-fueled portable heater having a flint-type igniter and an external incandescing heating element to which the gas is fed through an adjustable valve. Incandescence continues until the gas flow to the heating element is shut off. A hinged perforated cover is located over the heating element so that the element cannot be touched but can supply heat through the perforations.

The invention itself, together with further objects and attendant advantages, will best be understood by reference to the following detailed description in connection with the accompanying drawings.

BRIEF DESCRIPTION OF THE DRAWINGS

FIG. 1 is an elevational schematic view of an embodiment of the invention;

FIG. 2 is a cross-sectional view of the fire-nozzle portion of the ignition means of the invention;

FIG. 3 is a cross-sectional view of the needle valve and on-off switch comprising the flow-control means of the invention;

DETAILED DESCRIPTION OF THE INVENTION

Figure 4:
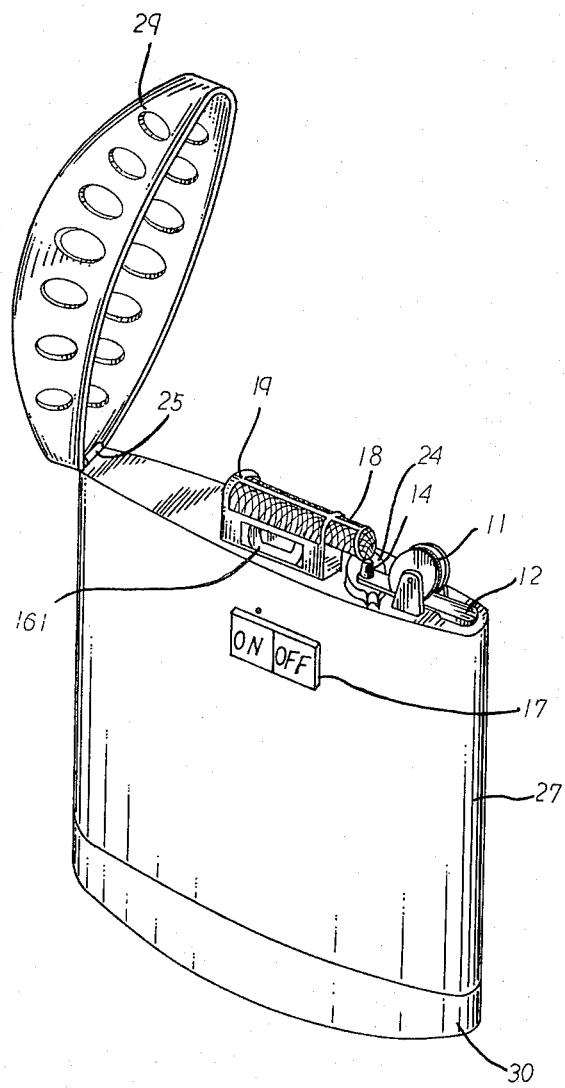
FIG. 4 is a perspective view of the gas heater.
Figure 5:
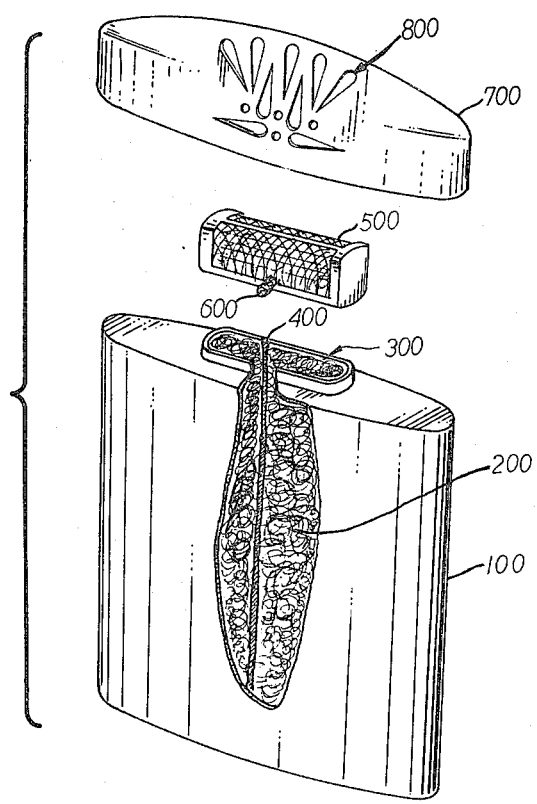
FIG. 5 is an exploded perspective view of the gas heater.

As shown in FIG. 1, there is an elevational schematic view of an embodiment of the invention, wherein a tank body 27 is a container having an empty tank space 23 which is filled with gas fuel through a filling hole 21. The ignition apparatus of the gas warmer comprises a spark-producing means and a flame-nozzle means. The spark-producing means comprises an external friction wheel 11 which is in contact with the top of a flint rod 13. The flint rod 13 is urged into contact with the friction wheel 11 by a spring 15 which is held in place by a screw in button 28. The flame-nozzle means comprises, as best seen in FIG. 2, an external flame nozzle 14, flame-adjusting button 24 and gas-switch pressure plate 12. The internal components comprise a capillary tube 142 leading to a sponge washer 141 which is located below a shut-off valve 144. A spring 143 normally urges the valve 144 into its closed position. Pressing down on the pressure plate 12 opens the valve 144, permitting the gas to flow through the capillary tube 142, sponge washer 141 and valve 144 to the flame hole 145 in the nozzle 14. Turning the flame-adjusting button 24 acts to control the density of the sponger washer and thus controls the rate of flow of gas to the nozzle 14.

The heating means of the gas warmer comprises: a gas inlet pipe 16 in the gas tank 23 and on the upper section of the inlet pipe 16 is installed an on-off switch 17 controlled from the outside of the tank body 27 to turn the gas flow on or off. The inlet pipe 16 ends in an outlet branch pipe 161 external to the top of tank body 27 and placed in a seat 20. The lower end of the inlet pipe 16 sits on the needle 21 of a needle valve, the vertical position of the needle 221 being controlled by a screw-in button 22 at the bottom of the tank body 27. Turning the button 22 inward advances the needle 22 to reduce and finally cut off the flow of gas through the inlet pipe 16. A seat cover 19 is placed over the seat 20 by a friction fit and retains a metallic cotton, incandescing heating element 18 having a tubular shape. The heating element is held so that one end is located over the frame nozzle 14. A perforated cover 29 is fastened by a hinge 25 to the top of the tank body at the end opposite the end at which the flame nozzle 14 is located.

When friction wheel 11 is quickly rotated bearing against flint 13 while the pressure plate 12 is depressed, sparks are struck from the flint. Fire nozzle 14 will produce a flame which heats the metal cotton 18 and makes it incandesce. If the pressure plate 12 is released, the flame is extinguished but the metal cotton heating element 18 is still incandescent. The switch 17 is turned to the on position and the outlet branch pipe 161 under metal cotton 18 supplies gas to keep metal cotton 18 red hot continuously. The gas volume is then adjusted by button 22 to control the temperature.

I claim:

1. A portable gas warmer comprising:
   a tank body for holding combustible gas fuel;
   ignition means mounted on said tank body for utilizing gas stored in said tank body as fuel to produce an ignition flame;
   heating means mounted on said tank body for contact with an ignition flame, said heating means being formed from a material which heats to incandescence by contact with said flame;
   gas-feeding means for transferring gas from said tank body to said heating means to maintain said heating means in incandescent condition when the ignition flame is turned off, said gas-feeding means including flow-control means for turning on or shutting off the flow of gas and means for controlling the rate of flow of said gas.

2. The invention defined in claim 1 wherein said heating element is fabricated from metallic cotton.

* * * * *